(12) United States Patent
Wang et al.

(10) Patent No.: US 10,487,023 B2
(45) Date of Patent: Nov. 26, 2019

(54) PRODUCTION OF NEOPENTANE

(71) Applicant: ExxonMobil Chemical Patents Inc., Baytown, TX (US)

(72) Inventors: Kun Wang, Bridgewater, NJ (US); Lorenzo C. DeCaul, Langhorne, PA (US); Michele L. Paccagnini, Randolph, NJ (US); Etienne Mazoyer, Woluwe Saint Pierre (BE); James R. Lattner, La Porte, TX (US); Helge Jaensch, Grimbergen (BE); Ali A. Kheir, Houston, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 16/324,722

(22) PCT Filed: Aug. 18, 2017

(86) PCT No.: PCT/US2017/047586
§ 371 (c)(1),
(2) Date: Feb. 11, 2019

(87) PCT Pub. No.: WO2018/044592
PCT Pub. Date: Mar. 8, 2018

(65) Prior Publication Data
US 2019/0169092 A1  Jun. 6, 2019

Related U.S. Application Data

(60) Provisional application No. 62/380,519, filed on Aug. 29, 2016.

(51) Int. Cl.
C07C 4/08  (2006.01)
C07C 5/27  (2006.01)
C07C 4/10  (2006.01)
C07C 7/04  (2006.01)
C07C 9/18  (2006.01)

(52) U.S. Cl.
CPC .............. C07C 4/10 (2013.01); C07C 5/2705 (2013.01); C07C 5/2708 (2013.01); C07C 7/04 (2013.01); C07C 5/277 (2013.01); C07C 9/18 (2013.01); C07C 2521/08 (2013.01); C07C 2523/42 (2013.01); C07C 2523/46 (2013.01); C07C 2523/755 (2013.01); C07C 2527/10 (2013.01); C07C 2527/12 (2013.01)

(58) Field of Classification Search
CPC ....... C07C 4/08; C07C 5/2213; C07C 5/2253; C07C 5/27
USPC ................ 585/310, 734, 741, 750, 751, 752
See application file for complete search history.

(56) References Cited

U.S. PATENT DOCUMENTS

| | | | |
|---|---|---|---|
| 2,325,052 A | 7/1943 | Grosse et al. | |
| 2,394,743 A | 2/1946 | Bergsteinsson | |
| 2,413,691 A | 1/1947 | Crawford et al. | |
| 2,422,670 A | 6/1947 | Haensel et al. | |
| 2,422,672 A | 6/1947 | Haensel et al. | |
| 2,422,674 A | 6/1947 | Haensel et al. | |
| 2,422,675 A | 6/1947 | Haensel et al. | |
| 2,436,923 A | 3/1948 | Haensel et al. | |
| 2,443,608 A * | 6/1948 | Evering | C07C 5/2789 585/745 |
| 3,585,252 A | 6/1971 | Kennedy | |
| 3,660,516 A | 5/1972 | Crain et al. | |
| 3,755,493 A | 8/1973 | Norel | |
| 3,855,346 A | 12/1974 | Norel | |
| 4,593,147 A | 6/1986 | Butter et al. | |
| 4,940,829 A | 7/1990 | Drake | |
| 5,146,037 A | 9/1992 | Zarchy et al. | |
| 6,262,192 B1 | 7/2001 | Wu | |
| 2007/0043247 A1 | 2/2007 | Webber et al. | |
| 2010/0210888 A1 * | 8/2010 | Taylor | C07C 5/2791 585/734 |

FOREIGN PATENT DOCUMENTS

| | | |
|---|---|---|
| GB | 574694 | 1/1946 |
| GB | 1220015 | 4/1967 |
| WO | 2018/044591 | 3/2018 |
| WO | 2018/044592 | 3/2018 |
| WO | 2018/044596 | 3/2018 |

OTHER PUBLICATIONS

Clarke et al., "The Preparation and Activity for Alkane Reactions of Aerosil-Supported Rhodium-Copper Clusters," Journal of Catalysis, vol. 111, pp. 374-382 (1988).
Haensel et al., "Selective Demethylation of Paraffin Hydrocarbons: Preparation of Triptane and Neopentane," Industrial and Engineering Chemistry, vol. 39, pp. 853-857 (1947).
Foger et al., "Skeletal Reactions of Hydrocarbons over Supported Iridium-Gold Catalysts," Journal of Catalysis, vol. 64, pp. 448-463 (1980).
Vogelzang et al., "Reactions of 2,2-Dimethylbutane on Iridium: The Role of Surface Carbonaceous Layers and Metal Particle Size," Journal of Catalysis, vol. 111, pp. 77-87 (1988).
Machiels, et al., "Hydrogenolysis of 2,2-Dimethylbutane and n-Hexane over Supported Ruthenium, Nickel, Cobalt, and Iron," Journal of Catalysis, vol. 58, pp. 268-275 (1979).
Leclercq et al., "Hydrogenolysis of Saturated Hydrocarbons: Influence of Hydrocarbon Structures on the Activity and Selectivity of Nickel on Silica," Journal of Catalysis, vol. 99, pp. 1-11.
Birkhoff et al., "NExOCTANE™ Technology for Isooctane Production," in Handbook of Petroleum Refining Processes, Third Edition, Ch. 1.1 (2004).
Kranz, K., "Alkylation chemistry-Mechanism, operating variables, and olefin interactions", DuPont Company, 2003.

(Continued)

Primary Examiner — Thuan D Dang

(57) ABSTRACT

Disclosed herein are processes for producing neopentane. The processes generally relate to demethylating neohexane and/or neoheptane to produce neopentane. The neohexane and/or neoheptane may be provided by the isomerization of $C_6$-$C_7$ paraffins.

20 Claims, 1 Drawing Sheet

(56) References Cited

OTHER PUBLICATIONS

Zimmer, H. et al., "Hydrogenolysis of alkanes with quaternary carbon atoms over Pt and Ni black catalysts", J.Chem. Soc., Fararday Trans. 1, 1982.
Graves, "STRATCO Effluent Refrigerated H2SO4 Alkylation Process," in Handbook of Petroleum Refining Processes, Third Edition, ch. 1.2 (2004).
Roeseler, "UOP AlkyleneTM Process for Motor Fuel," in Handbook of Petroleum Refining Processes, Third Edition, ch. 1.3 (2004).
Himes et al., "UOP HF Alkylation Technology," in Handbook of Petroleum Refining Processes, Third Edition, ch. 1.2 (2004).
Cusher, "UOP Penex Process," Handbook of Petroleum Refining Processes, Third Edition, Ch. 9.3 (2004).
Matsumoto et al., "Contrast between nickel and platinum catalysts in hydrogenolysis of saturated hydrocarbons," Journal of Catalysis, vol. 19(2), p. 101 (1970).
Matsumoto et al., "The classification of metal catalysts in hydrogenolysis of hexane isomers," Journal of Catalysis, vol. 22, pp. 182-192 (1971).
Paál et al, "On the pattern of hydrogenolysis of hexane isomers over four Group VIIIB metals," Reaction Kinetics and Catalysis Letters, vol. 12(2), pp. 131-137 (1979).
Richardson J. et al , "Preparation variables in nickel catalysts", J. Catal. 54, 207-218, 1978.
Schepers F.J., "Apparent particle size sensitivity in hydrocarbon reactions," J. Catal. 96, 82-87, 1985.
Richardson J. et al., "Crystallite Size Distributions and Stabilities of Homogeneously Deposited Ni/SiO2 Catalysts," Stu. Surf. Sci. Catal. 3, 131-142, 1979.
Coenen J., "Catalytic hydrogenation of fatty oils," Ind. Eng. Chem. Fundamen. 25 (1) 43-52, 1986.
Song C. et al., "Properties of the Ni/Kieselguhr catalysts prepared by precipitation method," Korean J. of Chem. Eng. 9 (3) 159-163, 1992.
Mendioroz S. et al., "Effect of the method of preparation on the activity of nickel Kieselguhr catalyst for vegetable oil hydrogenation," Appl. Catal. 66, 73-90, 1990.
Hadley, G.R., "Thermal conductivity of packed metal powders," International Journal of Heat and Mass Transfer 29.6, 909-920, 1986.
Avdonina, E.N., "Reactions of tritium recoil atoms in liquid mixtures of isooctane with benzene," XP002768312 & vol. 15, No. 5, 1973, pp. 720-726.
Zidek, Zdeno et al., "Nickel-silica-alumina catalysts. III. Catalytic properties. Hydrocracking of isooctane", 1969.
Seth et al., "Selective hydrogenation of 1,3-butadiene in mixture with isobutene on a Pd/@a-alumina catalyst in a semi-batch reactor", vol. 62, No. 17, 2007.

* cited by examiner

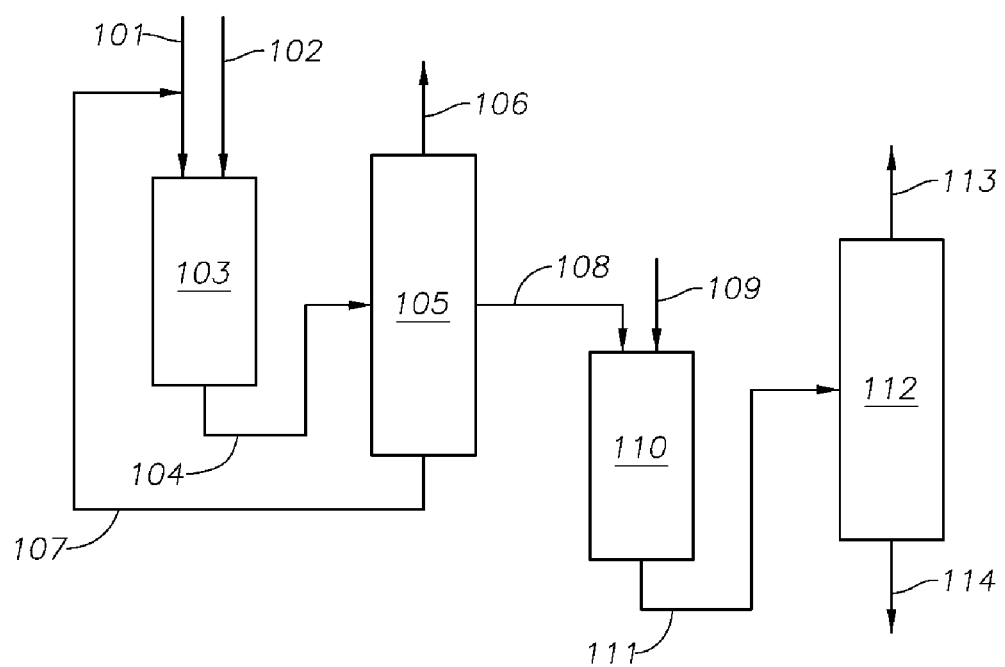

PRODUCTION OF NEOPENTANE

CROSS REFERENCES TO RELATED APPLICATIONS

This invention is a National Phase Application claiming priority to PCT Application Serial No. PCT/US2017/047586 filed Aug. 18, 2017, which claims priority to and benefit of U.S. Ser. No. 62/380,519, filed Aug. 29, 2016 and EP 16194990.4, filed Oct. 21, 2016, the disclosures of which are incorporated by reference.

FIELD OF THE INVENTION

The present invention relates to methods of producing neopentane and uses thereof.

BACKGROUND OF THE INVENTION

Neopentane is a unique nonpolar hydrocarbon molecule that has found industrial use in the form of an inert condensing agent for gas-phase reactions. See, for instance, U.S. Pat. No. 6,262,192. Other potential industrial uses for neopentane include use as a heat removal agent, a blowing agent, and a gasoline blend component due to its relatively high octane numbers. For instance, neopentane has a Research Octane Number (RON) of 85.5 and a Motor Octane Number (MON) of 80.2.

Currently, there is no satisfactory process for producing neopentane on a commercial scale. For example, typical existing processes for synthesizing neopentane utilize stoichiometric reactions of t-butylchloride and a Grignard reagent, methyl aluminum dichloride, dimethyl aluminum chloride, or trimethyl aluminum. See, for instance, U.S. Pat. No. 3,585,252. Such stoichiometric reactions generate large amounts of metal halides and are difficult to scale up to produce neopentane at commercial quantities. Likewise, though neopentane may be synthesized by hydrogenation of neopentanoic acid under high pressure and at high temperature, e.g., as described in U.S. Pat. No. 4,593,147, such processes are expensive due to the neopentanoic acid feedstock and suffer from a combination of demanding reaction conditions and low selectivity.

Other proposed processes for producing neopentane involve demethylation of higher carbon number branched paraffins. For example, U.S. Pat. Nos. 4,940,829 and 2,422,675 each relate to the preparation of neopentane via catalytic demethylation of neohexane. However, these higher carbon number branched paraffins are not readily available in high concentrations suitable as feedstock that could be utilized on a commercial scale.

Yet alternatively, a process for producing neopentane by hydrogenating an isobutylene polymer and selectively cracking the hydrogenation product is described in U.S. Pat. No. 2,394,743. However, in addition to producing neopentane, this process also produces large amounts of heavier hydrocarbon components.

Thus, there remains a need for processes for producing neopentane at high yield under mild reaction conditions and utilizing low cost, readily available feedstock. Such processes would allow economic production of neopentane at commercial quantities.

Other references of interest include: "The Preparation and Activity for Alkane Reactions of Aerosil-Supported Rhodium-Copper Clusters," Clarke et al., *Journal of Catalysis*, vol. 111, pp. 374-82 (1988); "Selective Demethylation of Paraffin Hydrocarbons: Preparation of Triptane and Neopentane," Haensel et al., *Industrial and Engineering Chemistry*, vol. 39, pp. 853-57 (1947); "Skeletal Reactions of Hydrocarbons over Supported Iridium-Gold Catalysts," Foger et al., *Journal of Catalysis*, vol. 64, pp. 448-63 (1980); "Reactions of 2,2-Dimethylbutane on Iridium: The Role of Surface Carbonaceous Layers and Metal Particle Size," Vogelzang et al., *Journal of Catalysis*, vol. 111, pp. 77-87 (1988); "Hydrogenolysis of 2,2-Dimethylbutane and n-Hexane over Supported Ruthenium, Nickel, Cobalt, and Iron," Machiels, et al., *Journal of Catalysis*, vol. 58, pp. 268-75 (1979); "Hydrogenolysis of Saturated Hydrocarbons: Influence of Hydrocarbon Structures on the Activity and Selectivity of Nickel on Silica," *Journal of Catalysis*, Leclercq et al., vol. 99, pp. 1-11; GB 574694; U.S. Pat. Nos. 2,422,670; 2,436,923; and "UOP Penex Process," in Handbook of Petroleum Refining Processes, Third Edition, Cusher, Ch. 9.3 (2004).

SUMMARY OF THE INVENTION

The present invention relates to novel processes that address the need for the production of neopentane at high yield, under mild reaction conditions, and utilizing readily available feedstock. The present invention relates to a process for producing neopentane comprising isomerizing $C_6$-$C_7$ paraffins to produce neohexane or neoheptane, followed by demethylating the neohexane or neoheptane to produce a product comprising at least 40 wt % neopentane. Typically, the $C_6$-$C_7$ paraffins can be provided in a $C_4$-$C_7$ paraffinic feed stream, preferably a light virgin naphtha stream.

BRIEF DESCRIPTION OF THE DRAWINGS

The FIGURE is a diagram of a process of neopentane.

DETAILED DESCRIPTION OF THE EMBODIMENTS

Described herein are processes for producing neopentane. As discussed below, the processes involve the demethylation of neohexane and/or neoheptane, preferably via contacting the neohexane or neoheptane with hydrogen in the presence of a catalyst. The neohexane and/or neoheptane can be provided by isomerization, preferably catalytic isomerization, of $C_6$-$C_7$ paraffins. Preferably, the $C_6$-$C_7$ paraffins are provided in a $C_4$-$C_7$ paraffinic feed stream, such as a light virgin naphtha stream. Preferably, the processes described herein enable the production of neopentane in quantities of greater than about 5 kg/hr, preferably greater than about 500 kg/hr, preferably greater than about 5000 kg/hr, and preferably greater than about 35000 kg/hr.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a fractionation column" include embodiments where one, two or more fractionation columns are used, unless specified to the contrary or the context clearly indicates that only one fractionation column is used. Likewise, "a $C_{12}+$ component" should be interpreted to include one, two or more $C_{12}+$ components unless specified or indicated by the context to mean only one specific $C_{12}+$ component.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first feedstock are expressed based on the total weight of the first feedstock. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

As used herein, "hydrocarbon" refers to molecules or segments of molecules containing primarily hydrogen and carbon atoms. As used herein, the term "$C_n$" hydrocarbon wherein n is a positive integer, e.g., 1, 2, 3, 4, etc., means a hydrocarbon having n number of carbon atom(s) per molecule. The term "$C_n+$" hydrocarbon wherein n is a positive integer, e.g., 1, 2, 3, 4, etc., as used herein, means a hydrocarbon having at least n number of carbon atom(s) per molecule. The term "$C_n-$" hydrocarbon wherein n is a positive integer, e.g., 1, 2, 3, 4, etc., used herein, means a hydrocarbon having no more than n number of carbon atom(s) per molecule.

As used herein, "olefin" refers to any unsaturated hydrocarbon having the formula $C_nH_{2n}$ and containing one carbon-carbon double bond, wherein C is a carbon atom, H is a hydrogen atom, and n is the number of carbon atoms in the olefin.

As used herein, "alkane" or "paraffin" refers to any saturated hydrocarbon having the formula $C_nH_{2n+2}$, wherein C is a carbon atom, H is a hydrogen atom, and n is the number of carbon atoms in the alkane. As used herein, "normal" paraffins, signified by the prefix "n," are linear, straight-chain paraffins. As used herein, "isoparaffins," signified by the prefix "i-," are branched paraffins.

As used herein, a "primary carbon atom" refers to a carbon atom neighboring one carbon atom, "secondary carbon atom" refers to a carbon atom neighboring two carbon atoms, "tertiary carbon atom" refers to a carbon atom neighboring three carbon atoms, and "quaternary carbon atom" refers to a carbon atom neighboring four carbon atoms.

As used herein, the prefix "normal" or "n-" signifies a linear unbranched hydrocarbon.

As used herein, the prefix "iso" or "i-" signifies a hydrocarbon containing a methyl substitution at the second carbon of the hydrocarbon chain.

As used herein, the prefix "neo" signifies a hydrocarbon containing a quaternary carbon atom. For example, the term "neopentane" refers to a compound of the formula $C_5H_{12}$ and containing a quaternary carbon atom, otherwise known as 2,2-dimethylpropane.

As used herein, "Lewis acid" refers to a molecule, species, ion, or radical that is electron deficient and, therefore, is capable of accepting a pair of electrons from a donor species.

Isomerization of $C_6$-$C_7$ Paraffins

Often, neohexane and/or neoheptane is formed in the present invention by the isomerization of $C_6$ paraffins (e.g., n-hexane, i-hexane, or 2,3-dimethylbutane) and/or $C_7$ paraffins, (e.g., n-heptane, i-heptane, 2,4-dimethylpentane, or 2,3-dimethylpentane) preferably via contacting the $C_6$-$C_7$ paraffins with hydrogen in the presence of a catalyst. Preferably, the $C_6$-$C_7$ paraffins are provided in a $C_4$-$C_7$ paraffinic feed stream. Suitable $C_4$-$C_7$ paraffinic feed streams include substantially pure normal paraffin streams having from 4 to 7 carbon atoms or a mixture of such substantially pure normal paraffins, light natural gasoline, light virgin naphtha, light straight run naphtha, gas oil condensate, light raffinates, light reformate, light hydrocarbons, and straight run distillates having distillation end points of about 98° C. (210° F.) and containing substantial quantities of $C_4$-$C_7$ paraffins. The $C_4$-$C_7$ paraffinic feed stream preferably comprises a light virgin naphtha stream.

Often, the $C_4$-$C_7$ paraffinic feed stream comprises about 50 wt % or more of $C_4$-$C_7$ paraffinic hydrocarbons, such as from about 50 wt % to about 90 wt % or from about 70 wt % to about 80 wt % by weight of the paraffinic feed. Generally, the $C_4$-$C_7$ paraffins are primarily linear aliphatics. However, naphthenes (cycloaliphatic hydrocarbons) may be present in the $C_4$-$C_7$ paraffinic feed stream up to about 20 wt %, such as from about 2 wt % to about 20 wt % by weight of the paraffinic feed. Typically, the $C_4$-$C_7$ paraffinic feed stream may also comprise: up to about 10 wt % of olefinic hydrocarbons, such as from about 1 wt % to about 5 wt %; and up to about 20 wt % of $C_{8+}$ hydrocarbons, such as from about 5 wt % to about 15 wt %, each by weight of the paraffinic feed (100 wt %). Preferably, the concentration of the olefinic hydrocarbons and $C_{8+}$ hydrocarbons is minimized to reduce hydrogen consumption and inhibit undesired cracking reactions. Often, the $C_4$-$C_7$ paraffinic feed is pretreated to remove aromatics and sulfur. Preferably, the pretreated $C_4$-$C_7$ paraffinic feed contains no more than a maximum of about 0.1 wt % of aromatics and no more than a maximum of about 0.001 wt % sulfur based on the weight of paraffinic feed. Optionally, the $C_4$-$C_7$ paraffinic feed may be further pretreated to remove $C_8+$ hydrocarbons.

Typically, the isomerization is conducted in the presence of a catalyst. Any catalyst suitable for paraffin isomerization, whether homogeneous or heterogeneous, may be used. Preferred catalysts are of two types: Lewis acids and bifunctional catalysts. Suitable Lewis acids include aluminum and boron halides (e.g., boron trifluoride, aluminum chloride, and chlorided alumina), strong acids (e.g., hydrochloric acid, hydrofluoric acid), and mixtures thereof (e.g., aluminum chloride and hydrochloric acid). Suitable bifunctional catalysts generally comprise a transition metal component and a solid acid component. Suitable transition metal components include Pd, Pt, Rh, Ru, Os, Ir, Au, Ag, Cu, Ni, Co, Fe, and Re, combinations thereof, compounds thereof, and mixtures of compounds thereof, with Pt being particularly preferred. Suitable solid acid components include zeolites, amorphous aluminosilicates, acidic metal oxides or mixed metal oxides, solid phosphoric acid, and mixtures thereof. Non-limiting examples of such zeolites include those of the MFI framework type (e.g., ZSM-5), zeolite beta, mordenite, faujasite, and those of the MWW family (e.g., MCM-22, -49, or -56), especially those such zeolites having a high silicon to aluminum ratio (Si/Al), conveniently greater than 20:1, such as 50:1 or 100:1. Non-limiting examples of acidic metal oxides or mixed metal oxides includes tungsten oxides ($WO_x$), molybdenum oxide ($MoO_x$), mixed oxides such as $WO_x/ZrO_2$, $WO_x/CeO_2$, $MoO_x/ZrO_2$, $MoO_x/CeO_2$, and sulfated zirconia.

The isomerization reaction can be conducted in a wide range of reactor configurations including fixed bed (single or in series), slurry reactors, and/or catalytic distillation towers. In addition, the isomerization reaction can be conducted in a single reaction zone or in a plurality of reaction zones. Suitable reaction temperatures are generally below about 300° C. to thermodynamically favor the production of neohexane and neoheptane, such as from about 25° C. to 300° C., or from about 50° C. to about 250° C., or from about 100° C. to about 250° C. Preferably, the reaction pressure is maintained so that the $C_4$-$C_7$ paraffinic feed remains in gas form within the reactor. For instance, suitable reaction pressures are from about 100 kPa absolute and about 10000 kPa absolute (e.g., from about 15 psia to about 15000 psia), such as between about 500 kPa absolute and about 5000 kPa absolute. Preferably, the isomerization is conducted at a hydrogen partial pressure of less than about 5000 kPa absolute, preferably less than about 2500 kPa absolute, and preferably less than about 1000 kPa absolute (e.g., preferably less than about 750 psia absolute, preferably less than about 370 psia absolute or preferably less than about 150 psia absolute).

Demethylation of Neohexane and/or Neoheptane

The major components of the isomerization reaction effluent are generally neohexane and/or neoheptane, unreacted normal paraffin components of the $C_4$-$C_7$ paraffinic feed, non-neo $C_4$-$C_7$ branched paraffins (e.g., i-pentane, i-hexane, i-heptane, 2,4-dimethylpentane, and 2,3-dimethylpentane), and $C_3$– hydrocarbon components obtained as a result of side cracking reactions. Using a hexanes feed as an example, the primary $C_5$-$C_6$ paraffin constituents of the isomerization reaction effluent, along with each of their boiling points, are summarized in Table 1.

TABLE 1

| Component | Boiling Point (° C.) |
| --- | --- |
| n-pentane | 36 |
| i-pentane | 27.7 |
| neopentane | 9.5 |
| n-hexane | 69 |
| 2-methyl pentane (i-hexane) | 62 |
| 3-methyl pentane | 64 |
| 2,3-dimethyl butane | 58 |
| neohexane | 50 |

The unreacted feed components, $C_4$-$C_7$ isoparaffins, and $C_3$– hydrocarbon components can be readily removed from the reaction effluent by, for example, distillation. The remainder of the isomerization reaction effluent, mainly composed of neohexane and/or neoheptane, can be demethylated to produce neopentane. Preferably, the separated isomerization reaction effluent comprises greater than about 80 wt % neohexane and/or neoheptane, or greater than about 90 wt % neohexane and/or neoheptane, or greater than about 95 wt % neohexane and/or neoheptane, or greater than about 99 wt % neohexane and/or neoheptane, such as from about 90 wt % to about 100 wt % neohexane and/or neoheptane, or from about 95 wt %, to about 99 wt % neohexane and/or neoheptane.

Preferably, the demethylation is conducted via demethylation by contacting the neohexane and/or neoheptane with hydrogen in the presence of a catalyst. The desired demethylation of the neohexane and/or neoheptane may be summarized in the following reaction scheme:

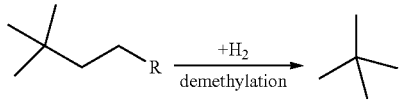

Where R is H for neohexane and $CH_3$ for neoheptane. As shown from the reaction scheme above, the desired demethylation occurs at the secondary (2°) carbon of the neohexane or neoheptane. Competing demethylation can occur at the quaternary (4°) carbon. Advantageously, demethylation at the quaternary (4°) carbon in the present processes is minimized to prevent a loss of neopentane yield.

The demethylation reaction can be conducted in a wide range of reactor configurations including fixed bed (single or in series), slurry reactors, and/or catalytic distillation towers. In addition, the demethylation reaction can be conducted in a single reaction zone or in a plurality of reaction zones. The demethylation is conveniently conducted at a temperature from about 200° C. to about 500° C., such as from about 300° C. to about 400° C. and a pressure from about 100 kPa absolute to about 10000 kPa absolute (e.g., atmospheric to about 1500 psia), such as from about 300 kPa absolute to about 8000 kPa absolute, in the presence of a catalyst. Often, the demethylation is conducted at a hydrogen partial pressure of from about 50 kPa absolute to about 3500 kPa absolute (e.g., from about 7 psia to about 500 psia). Preferably, the demethylation is conducted at a hydrogen partial pressure of less than about 2500 kP absolute a, preferably less than about 2200 kPa absolute, and preferably less than about 1000 kPa absolute (e.g., preferably less than about 350 psia, or preferably less than about 150 psia). Particularly preferably, the demethylation may be conveniently conducted under conditions comprising one or more of the following: a temperature from about 220° C. to about 300° C.; a pressure from about 15 psig to about 200 psig (e.g., from about 205 kPa absolute to about 1400 kPa absolute); and a hydrogen to hydrocarbon molar ratio from about 1:1 to about 14:1.

Generally, the catalyst employed in the demethylation comprises a transition metal component. Specific, non-limiting examples of suitable transition metal components include Fe, Co, Ni, Rh, Ir, Ru, Pt, and Pd, combinations thereof, compounds thereof, and mixtures of compounds thereof, with Ni being particularly advantageous. Often, the transition metal component contains transition metal as a single component. Alternatively, the transition metal component may contain a transition metal combined with an additional metal to form a binary or ternary alloy. Specific, non-limiting examples of suitable additional metals include Cu, Au, Ag, Sn, Zn, Re, combinations thereof, compounds thereof, and mixtures of compounds thereof. Desirably, the amount of the transition metal component present in the catalyst is from about 0.05 wt % to about 60.0 wt %, such as from about 0.10 wt % to about 50.0 wt %, of the total weight of the catalyst. Generally, the transition metal component is supported on a non-acidic support material. Specific, non-limiting examples of suitable support materials include silica, theta-alumina, clay, pentasil, aluminophosphate, carbon, titania, zirconia, and mixtures thereof.

Preferably, the acidity of the catalyst employed in the demethylation is minimized to inhibit undesired cracking reactions. Often, the acidity of the catalyst is reduced via impregnation with an alkali metal compound, preferably an alkali metal hydroxide, nitrate, carbonate, bicarbonate, or oxide, such as sodium oxide, e.g., $Na_2O$. Desirably, the amount of the alkali metal compound present in the catalyst is from about 0.05 wt % to about 1.0 wt %, such as from about 0.1 wt % to about 0.5 wt %, of the total weight of the catalyst.

Typically, the neohexane and/or neoheptane conversion during the demethylation step is greater than 80%, preferably greater than 90%, preferably greater than 95%, and preferably greater than 99%, such as from 80% to 99% or 90 to 99%. The product of the demethylation step generally comprises neopentane and $C_4-$ hydrocarbon components (e.g., methane, ethane, and propane). Preferably, the product of the demethylation step comprises: at least about 40 wt %, preferably at least about 50 wt %, preferably at least about 60 wt %, and ideally at least about 70 wt % of neopentane, such as from about 40 wt % to about 70 wt % or from about 50 wt % to about 65 wt %; less than about 50 wt %, preferably less than about 40 wt %, and preferably less than about 30 wt % of $C_4-$ hydrocarbon components such as from about 30 wt % to about 50 wt % or from about 35 wt % to about 45 wt %; and less than about 5 wt %, preferably less than about 1 wt %, and ideally less than about 0.5 wt % of non-neopentane $C_5$ hydrocarbon components, such as from about 0 wt % to about 1 wt % or from about 2 wt % to about 5 wt %. Preferably, the demethylation of neohexane and/or neoheptane exhibits high single-pass yields of neopentane. For example, typically the single-pass yield of neopentane in the demethylation of neohexane and/or neoheptane may be greater than about 40 wt %, preferably greater than about 50 wt %, and ideally greater than about 60 wt %. In such aspects, the demethylation step can be conveniently conducted in the absence of recycle, i.e., without recycling any portion of the demethylation product. Preferably, conducting the demethylation step without recycle provides several process advantages, such as increasing process reliability and reducing operating costs.

The light $C_4-$ hydrocarbon components can be readily removed from the demethylation product by, for example, distillation, thereby yielding a purified neopentane product stream. Preferably, the purified neopentane product stream comprises greater than about 80 wt % neopentane, or greater than about 90 wt % neopentane, or greater than about 95 wt % neopentane, or greater than about 99 wt % neopentane, such as from about 80 wt % to about 99 wt % neopentane, or from about 85 wt %, to about 95 wt % neopentane.

Process

The present inventive process will now be more particularly described with reference to the FIGURE. The FIGURE illustrates one aspect of the present inventive process, in which a $C_4-C_7$ paraffinic feed stream is fed to an isomerization reactor to produce an isomerization product, after which neohexane and/or neoheptane is separated and demethylated. The invention is not limited to this aspect, and this description is not meant to foreclose other aspects within the broader scope of the invention.

As shown in the FIGURE, a $C_4-C_7$ paraffinic feed stream 101 and a hydrogen stream 102 are fed to an isomerization reactor 103 to produce an isomerization effluent 104 comprising neohexane and/or neo-heptane, unreacted $C_4-C_7$ normal paraffins (e.g., n-pentane, n-hexane, and n-heptane), non-neo $C_4-C_7$ branched paraffins (e.g., i-pentane, i-hexane, i-heptane, 2,4-dimethylpentane, and 2,3-dimethylpentane), and $C_3-$ hydrocarbon components obtained from cracking reactions. The isomerization effluent is then fed to a separator 105, e.g., a distillation column, to separate a light fraction 106 comprising $C_5-$ hydrocarbons and a heavy fraction 107 comprising non-neo $C_6-C_7$ hydrocarbon isomers from the isomerization effluent. The resulting obtained fraction 108 is mainly composed of neohexane and/or neoheptane. Preferably, the light fraction 106 may be used for fuel or mogas (not shown). The heavy fraction 107 can be recycled to isomerization reactor 103. Fraction 108 and a hydrogen stream 109 are then introduced to a demethylation reactor 110 to produce a demethylation effluent 111 comprising neopentane and $C_4-$ hydrocarbons. The demethylation effluent 111 is then fed to a separator 112 e.g., a distillation column, to separate a light fraction 113 comprising $C_4-$ hydrocarbons from the demethylation effluent 111. The resulting obtained fraction 114 is mainly composed of neopentane. The light fraction 113 can be used for fuel (not shown).

Neopentane produced in accordance with the present invention is useful as a blowing agent for the production of foamed polymers and possesses several properties (e.g., a boiling point of 9.5° C. and a freezing point of −16.6° C.) making it useful as a heat removal agent and/or as an inert condensing agent (ICA) in gas phase polymerization process, such as gas phase polymerization processes for the production of polyethylene. Neopentane produced in accordance with this invention also exhibits high octane numbers and is therefore useful as a gasoline blend component.

The invention will now be more particularly described with reference to the following non-limiting Examples.

EXAMPLES

Example 1: Synthesis of 1.5% $Rh/SiO_2$ Demethylation Catalyst

A 1.5% $Rh/SiO_2$ catalyst was prepared by incipient wetness impregnation. Silica gel (Davisil™ 646, Sigma-Aldrich) was calcined by heating at a rate of 10° C./min to 700° C. and holding at 700° C. for 15 hours, then cooled to 50° C. and held at temperature overnight. The pore volume of the calcined silica was determined to be 1.34 cc/g. The calcined silica (10 g) was then impregnated with a solution of rhodium (III) chloride hydrate (0.39 g) dissolved in 13.4 mL water to give an Rh loading of 1.5 wt %. The resultant product was transferred to a ceramic dish, calcined by heating at a rate of 10° C./min to 250° C. and holding at 250° C. for 10 hours, then cooled to 50° C. and held at temperature overnight.

Example 2: Synthesis of 1.5% $Ir/SiO_2$ Demethylation Catalyst

A 1.5% $Ir/SiO_2$ catalyst was prepared by incipient wetness impregnation. Silica gel (Davisil™ 646, Sigma-Aldrich) was calcined by heating at a rate of 10° C./min to 700° C. and holding at 700° C. for 15 hours, then cooled to 50° C. and held at temperature overnight. The pore volume of the calcined silica was determined to be 1.34 cc/g. An aqueous solution of iridium (III) chloride was prepared by adding 0.28 g of iridium (III) chloride hydrate to 13.4 mL water, followed by adding 5 drops of concentrated HCl. The resulting mixture was then stirred and heated until the metal salt completely dissolved. The calcined silica (10 g) was then impregnated with the prepared aqueous solution to give an Ir loading of 1.5 wt %. The resultant product was transferred to a ceramic dish, calcined by heating at a rate of 10° C./min to 250° C. and holding at 250° C. for 10 hours, then cooled to 50° C. and held at temperature overnight.

Example 3: Demethylation of Neohexane

A neohexane feed was demethylated in the presence of each of the catalyst of Example 1, the catalyst of Example 2, and a 1.5% Pd/SiO$_2$ catalyst using a down-flow, tubular, fixed bed reactor and process described below.

Catalytic reactions were performed using a down-flow, tubular, fixed-bed reactor equipped with two 100-mL ISCO pumps and various gas feeds. The liquid feed was delivered via the ISCO pumps, mixed with gas feed through a heated section for vaporization before entering the reactor (⅜ in O.D.×16¾ in×0.028 in wall stainless steel tube) (1 cm×43 cm×0.07 cm). Catalyst (0.25-2 g loading) was pelletized and sized to 20-40 mesh, diluted with quartz chips to a total volume of 5 mL and loaded in the isothermal zone of the reactor. A piece of ¼ in (0.6 cm) O.D. stainless steel tubing was inserted at the bottom of the reactor tube to ensure the catalyst bed being located in the isothermal zone of the furnace. Glass wool was used at the top and bottom of the catalyst bed to keep the catalyst bed in place. Reactor pressure was controlled via a research control valve (RCV) at the exit of the reactor and the reactor effluent was heat-traced and sent to a gas chromatograph (GC) for on-line analysis.

The catalyst was first purged with N$_2$ and then heated to 300° C.-500° C. at a ramp rate of 3° C./min under flowing H$_2$ (100 cc/min) and held 2-4 h for reduction. After reduction, the reactor was cooled down to the operating temperature. The liquid feed was then introduced and H$_2$ flow rate adjusted accordingly at the desired operating pressure.

An Agilent HP 7890™ GC having a Restek 30 m×0.32 mm×5 μm GC column (Rtx™-1, Catalog #10178) was used for product analysis. The injector was set at 260° C. and the detector at 280° C. The column flow rate was 1.2 cc/min He, with typical air and H$_2$ flows for the detector. The oven temperature was programmed in the following manner: initial temperature of 40° C.; hold for 5 min; ramp at 4° C./min to 200° C.; ramp at 20° C./min to 260° C. for bake out. The total reactor effluent was sampled and analyzed hourly. GC peaks were identified using the "Alphagaz PIANO Calibration Standards" (Supelco Product #4-4586-U, available from Sigma-Aldrich) and authentic samples, using a response factor of one for all components.

The theoretical neopentane yield using this described process and a neohexane feed was estimated to be ca. 80 wt %. The results of the GC testing of the reactor effluent at various reaction conditions are summarized in Table 2.

Example 4: Demethylation of Neohexane Using Ni/SiO$_2$ Catalyst with Varying Process Conditions The demethylation tests described in Examples 4A-4K were carried out in a reactor unit having eight modules serviced by communal gas and liquid feed lines. Each individual module featured independent temperature, pressure, and feed flow controls.

A Ni/SiO$_2$ catalyst (64 wt % Ni powder on silica, obtained from Strem Chemicals, Inc.) was pelletized, crushed, sieved (40-20 mesh, 840 to 400 μm), and loaded into each of the unit modules along with SiC diluent. The catalyst loading amount was varied depending on the desired WHSV of the isooctane feed. The catalyst was pre-conditioned in situ by heating to 400° C. with H$_2$ flow at 500 sccm/min at 30 psig (300 kPa absolute) and holding for 8 h.

An Agilent HP 7890 GC equipped with dual inlets (i.e., a front inlet and a rear inlet), two FID detectors, and two 60 m×250 μm×1.0 μm HP-1 GC columns (Agilent Technologies) located in parallel (corresponding to the front inlet and rear inlet, respectively) was used for online product analysis to determine the reported conversion and selectivity values. Modules 1-4 of the reactor unit were connected in series with the front inlet, and modules 5-8 of the reactor unit were connected to the rear inlet. Sample injection was enabled via a 250 μl sample loop that was connected to a Valco 6 port GC injection valve. In order to increase the sampling frequency, two simultaneous injections were done for both inlets.

The GC was operated in a ramped pressure and split mode using hydrogen as carrier gas and a split ratio of 100 to 1. The initial pressure was set at 20 psi (140 kPa) and held for 1.5 min, and then ramped at 7 psi/min (50 kPa/min) to a final pressure of 50 psi (340 kPa). The initial oven temperature was set at 35° C. and held for 2 min, and then ramped at 25° C./min to 250° C. The total analysis time was about 10.6 min, which enabled an injection every 15 min and a corresponding analysis frequency of 1 h per pair of modules.

In each of examples 4A-4K, the WHSV of the neohexane feed was varied in order to vary the residence time of the feed within the reactor. Results of the GC testing at varying process conditions (temperature, total pressure, hydrogen to hydrocarbon (H2:HC) molar ratio, and WHSV) are summarized in Table 3.

TABLE 2

[1.049 g catalyst, reduced at 400° C. (2 h, 100 cc/min H$_2$); Feed Liquid Weight Hourly Space Velocity (LWHSV) = 4 h$^{-1}$; H$_2$ Flow Rate = 142 cc/min; N$_2$ Flow Rate = 39 cc/min].

| | Conditions | | | Conversion and Selectivity | | | | | | |
|---|---|---|---|---|---|---|---|---|---|---|
| Catalyst | Temperature (° C.) | Pressure (psia) | Pressure (kPa absolute) | Neohexane Conversion (%) | Methane (wt %) | Ethane (wt %) | Propane (wt %) | C$_4$ (wt %) | Neopentane (wt %) | Other C$_5$- (wt %) |
| 1.5% Rh/SiO$_2$ | 250 | 30 | 200 | 66 | 19.56 | 3.24 | 2.60 | 7.96 | 62.71 | 3.88 |
| 1.5% Rh/SiO$_2$ | 300 | 30 | 200 | 98 | 30.34 | 10.58 | 1.95 | 6.16 | 50.90 | 0.06 |
| 1.5% Ir/SiO$_2$ | 250 | 30 | 200 | 39.8 | 16.5 | 4.5 | 1.1 | 8.5 | 66.9 | 2.3 |
| 1.5% Pd/SiO$_2$ | 300 | 30 | 200 | 86.3 | 23.2 | 5.9 | 1.5 | 9.1 | 60.7 | 0.3 |

TABLE 3

| Example | Temperature [° C.] | Total pressure [psig] | H2:HC [mol:mol] | WHSV [h−1] | Neohexane Conversion [%] | Neopentane Selectivity [wt %] |
|---|---|---|---|---|---|---|
| 4A | 240 | 100 | 4.5 | 4 | 23 | 71 |
| | | | | 5 | 17 | 71 |
| | | | | 6.67 | 14 | 70 |
| | | | | 10 | 9 | 70 |
| | | | | 13.33 | 6 | 69 |
| | | | | 20 | 4 | 67 |
| 4B | 240 | 45 | 4.5 | 4 | 69 | 68 |
| | | | | 5 | 51 | 69 |
| | | | | 6.67 | 39 | 70 |
| | | | | 10 | 23 | 70 |
| | | | | 13.33 | 16 | 70 |
| | | | | 20 | 11 | 70 |
| 4C | 240 | 50 | 2 | 4 | 42 | 71 |
| | | | | 5 | 31 | 72 |
| | | | | 6.67 | 17 | 71 |
| | | | | 10 | 20 | 71 |
| 4D | 240 | 50 | 5 | 5 | 25 | 69 |
| | | | | 7 | 19 | 69 |
| | | | | 12 | 11 | 68 |
| | | | | 15 | 9 | 67 |
| | | | | 30 | 5 | 64 |
| 4E | 240 | 50 | 7 | 2.67 | 66 | 68 |
| | | | | 4 | 39 | 69 |
| | | | | 5 | 32 | 69 |
| | | | | 6.67 | 23 | 70 |
| | | | | 10 | 17 | 69 |
| | | | | 13.33 | 11 | 69 |
| | | | | 20 | 8 | 69 |
| 4F | 240 | 150 | 2 | 2.67 | 50 | 70 |
| | | | | 4 | 24 | 71 |
| | | | | 6.67 | 14 | 70 |
| | | | | 10 | 9 | 68 |
| | | | | 13.33 | 6 | 66 |
| | | | | 20 | 4 | 64 |
| 4G | 260 | 50 | 2 | 10 | 21 | 69 |
| | | | | 15 | 28 | 69 |
| | | | | 17.5 | 28 | 68 |
| 4H | 260 | 50 | 3 | 5 | 63 | 64 |
| | | | | 7 | 33 | 70 |
| | | | | 12 | 17 | 69 |
| | | | | 15 | 25 | 69 |
| 4I | 260 | 50 | 5 | 30 | 12 | 68 |
| | | | | 35 | 18 | 67 |
| | | | | 40 | 16 | 67 |
| | | | | 45 | 15 | 67 |
| 4J | 260 | 50 | 7 | 20 | 30 | 68 |
| | | | | 23 | 25 | 68 |
| | | | | 25 | 23 | 68 |
| | | | | 27 | 21 | 68 |
| | | | | 30 | 20 | 67 |
| | | | | 35 | 16 | 67 |
| | | | | 40 | 15 | 67 |
| 4K | 260 | 100 | 15 | 1.67 | 76 | 66 |
| | | | | 3.33 | 49 | 68 |
| | | | | 5 | 36 | 68 |

From the data obtained in Examples 4A-4K, the absolute rates of the reactions producing the primary demethylation products and the relative rates of these reactions compared to others were regressed by comparing the selectivity of the demethylation products at the varied residence times and extrapolating these results to a zero residence time. The regressed absolute and relative reaction rates were then used to calculate simulated neopentane yields and production rates at a conversion of 80% in a theoretical demethylation process comprising demethylating a neohexane feed in a single-pass (i.e., without recycle). The obtained simulated neopentane yields and ratios of the simulated neopentane production rates relative to the simulated neopentane production rate of Example 4A at varying process conditions (temperature, total pressure, and hydrogen to hydrocarbon (H2:HC) molar ratio) are summarized in Table 4.

TABLE 4

| Example | Temperature (° C.) | Pressure (psig) | H2:HC (mol:mol) | Simulated Neopentane Yield at 80% Conversion (wt %) | Ratio of Simulated Neopentane Production Rate Relative to Simulated Neopentane Rate of Example 4A at 80% Conversion |
|---|---|---|---|---|---|
| 4A | 240 | 100 | 4.5 | 52 | 1.0 |
| 4B | 240 | 45 | 4.5 | 54 | 2.2 |
| 4C | 240 | 50 | 2 | 52 | 3.8 |
| 4D | 240 | 50 | 5 | 50 | 1.9 |
| 4E | 240 | 50 | 7 | 53 | 1.6 |
| 4F | 240 | 150 | 2 | 53 | 1.4 |

TABLE 4-continued

| Example | Temperature (° C.) | Pressure (psig) | H2:HC (mol:mol) | Simulated Neopentane Yield at 80% Conversion (wt %) | Ratio of Simulated Neopentane Production Rate Relative to Simulated Neopentane Rate of Example 4A at 80% Conversion |
|---|---|---|---|---|---|
| 4G | 260 | 50 | 2 | 53 | 12.1 |
| 4H | 260 | 50 | 3 | 53 | 8.2 |
| 4I | 260 | 50 | 5 | 50 | 6.0 |
| 4J | 260 | 50 | 7 | 53 | 5.2 |
| 4K | 260 | 100 | 15 | 53 | 1.9 |

As can be seen from Table 4, the simulated neopentane production rates varied significantly with changing process conditions, as expected. However, despite the wide variance in the simulated neopentane production rates, the simulated neopentane yield at 80% remained surprisingly near constant with respect to variances in each of temperature, pressure, and H2:HC ratio. These simulated results suggest that the demethylation step is surprisingly robust over the preferred process conditions comprising a temperature from about 220° C. to about 300° C.; a pressure from about 15 psig to about 200 psig (e.g., from about 205 kPa absolute to about 1400 kPa absolute); and/or a hydrogen to hydrocarbon molar ratio from about 1:1 to about 14:1.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A process for producing neopentane, the process comprising:
   (a) providing a feed stream including $C_6$-$C_7$ paraffins;
   (b) isomerizing the $C_6$-$C_7$ paraffins to produce an isomerization product including neohexane and/or neoheptane; and
   (c) demethylating the neohexane and/or neoheptane to produce a demethylation product including at least 40 wt % neopentane based on the weight of the demethylation product;
   wherein the demethylation comprises contacting the neohexane and/or neoheptane with hydrogen in the presence of a catalyst (B), wherein the catalyst (B) comprises at least one member selected from the group consisting of Fe, Co, Ni, Rh, Jr, Ru, Pt, Pd, combinations thereof, compounds thereof, and mixtures thereof; and further, wherein the catalyst (B) further comprises at least one member selected from the group consisting of Cu, Au, Ag, Sn, Zn, Re, combinations thereof, compounds thereof, and mixtures of compounds thereof.

2. The process of claim 1, wherein at least part of the neohexane and/or neoheptane is separated from the isomerization product prior to demethylation.

3. The process of claim 2, wherein separating the neohexane and/or neoheptane from the isomerization product comprises distillation.

4. The process of claim 3, wherein the isomerization product is separated into fractions comprising (1) a $C_5$-hydrocarbon fraction (2) a first $C_6$-$C_7$ hydrocarbon fraction comprising neohexane and/or neoheptane and (3) a second $C_6$-$C_7$ hydrocarbon fraction comprising non-neo isomers.

5. The process of claim 4, wherein the isomerization is carried out in a reaction vessel, and wherein the second $C_6$-$C_7$ hydrocarbon fraction is recycled to the reaction vessel.

6. The process of claim 1, wherein the feed stream comprises light virgin naphtha.

7. The process of claim 1, wherein the isomerization comprises contacting the feed stream with hydrogen in the presence of a catalyst (A).

8. The process of claim 7, wherein the catalyst (A) comprises at least one member selected from the group consisting of Pd, Pt, Rh, Ru, Os, Ir, Au, Ag, Cu, Ni, Co, Fe, Re, combinations thereof, compounds thereof, and mixtures of compounds thereof.

9. The process of claim 8, wherein the catalyst (A) comprises Pt.

10. The process of claim 8, wherein catalyst (A) further comprises a support material comprising at least one member selected from the group consisting of zeolites, amorphous aluminosilicate, acidic metal oxides or mixed metal oxides, solid phosphoric acid, and mixtures thereof.

11. The process of claim 7, wherein the catalyst (A) comprises at least one member selected from the group consisting of chlorided alumina, aluminum chloride, boron trifluoride, and mixtures thereof.

12. The process of claim 7, wherein the contacting is carried out at a temperature of less than about 300° C. and a hydrogen partial pressure of less than about 5000 kPa absolute (about 725 psia).

13. The process of claim 1, further comprising separating at least part of the neopentane from the demethylation product.

14. The process of claim 13, wherein separating the neopentane from the demethylation product comprises distillation.

15. The process of claim 14, wherein the demethylation product is separated into fractions comprising (1) a $C_4$-hydrocarbon fraction and (2) a neopentane fraction.

16. The process of claim 1, wherein the catalyst (B) comprises a support material selected from the group consisting of silica, theta-alumina, clay, pentasil, aluminophosphate, carbon, titania, zirconia, and mixtures thereof.

17. The process of claim 1, wherein the demethylation is carried out at a temperature of about 200° C. to about 500° C. and a hydrogen partial pressure of from about 50 kPa absolute to about 3500 kPa absolute (about 7 psia to about 500 psia).

18. The process of claim 1, wherein the demethylation is carried out under conditions comprising at least one of a temperature from about 220° C. to about 300° C., a pressure from about 15 psig to about 200 psig (about 205 kPa absolute to about 1400 kPa absolute), or a hydrogen to hydrocarbon molar ratio from about 1:1 to about 14:1.

19. The process of claim 1, wherein the single-pass yield of neopentane in the demethylation is greater than about 40 wt %.

20. The process of claim 1, wherein the demethylation product comprises greater than about 60 wt % neopentane based on the weight of the demethylation product.

* * * * *